United States Patent [19]

Miyake et al.

[11] Patent Number: 4,863,264
[45] Date of Patent: Sep. 5, 1989

[54] PHOTOANALYSIS APPARATUS WITH MEANS FOR CORRECTING FLOW RATE OF FLUID CARRYING PARTICLES AND/OR POSITION OF APPLIED LIGHT BEAM FOR EXAMINATION AND PHOTOANALYSIS METHOD THEREFOR

[75] Inventors: Ryo Miyake, Ibaraki; Hiroshi Ohki, Tsuchiura; Isao Yamazaki, Ibaraki, all of Japan

[73] Assignee: Hitachi, Ltd., Tokyo, Japan

[21] Appl. No.: 203,457

[22] Filed: Jun. 7, 1988

[30] Foreign Application Priority Data

Jun. 8, 1987 [JP] Japan ................................. 62-142775

[51] Int. Cl.⁴ ...................... G01N 33/48; G01N 21/64
[52] U.S. Cl. .................................... 356/39; 250/461.2; 356/72
[58] Field of Search ........................... 356/39, 72, 73; 250/461.2

[56] References Cited

U.S. PATENT DOCUMENTS 3,873,204  3/1975  Friedman et al. .................... 356/39
4,643,566  2/1987  Ohe et al. .............................. 356/72

OTHER PUBLICATIONS

Kamentsky et al, "Spectrophotometer: New Instrument for Ultrarapid Cell Analysis", Science, vol. 150, pp. 630-631, Oct. 1965.
Eisert, "Sample Flow Microphotometer for Rapid Cell Population Analysis", Rev. Sci. Instrum., vol. 46, No. 5, pp. 1021-1024, Aug. 1975.

Primary Examiner—Vincent P. McGraw
Attorney, Agent, or Firm—Antonelli, Terry & Wands

[57] ABSTRACT

A photoanalysis apparatus includes marker pouring device for pouring markers into one of sheath fluid and fluid carrying particles in a flow-cell device, second optical device for applying a light beam for correction to the markers in the flow-cell device to measure strength of fluorescence or light scattering caused by said markers to generate a signal for correction, second signal processing device for calculating from the signal for correction at least one of a difference in position between a center of the fluid carrying particles in the flow-cell device and a center of a light beam for examination and a difference in flow rate between a predetermined flow rate and an actual flow rate of the fluid carrying particles in the flow-cell device to generate correspondingly at least one of a first command signal for position correction and a second command signal for flow rate correction, and correspondingly at least one of first correcting device for shifting the center of the light beam for examination to the center of the flow of the fluid carrying particles in accordance with the first command signal and second correcting device for correcting the flow rate of the fluid carrying particles to the predetermined flow rate in accordance with the second command signal.

7 Claims, 12 Drawing Sheets

FIG. 4-1-a
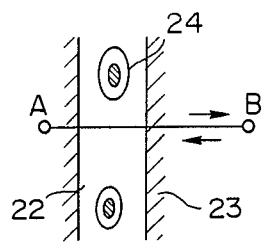
FIG. 4-1-b
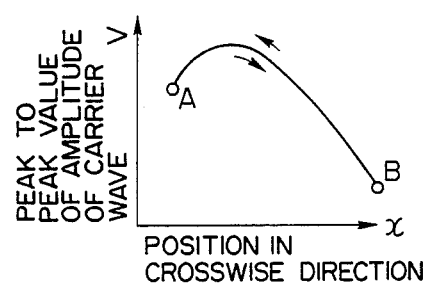
FIG. 4-1-c
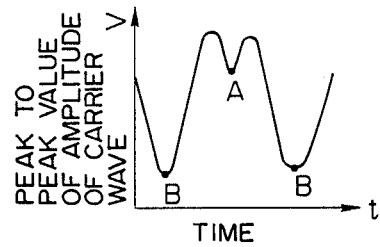
FIG. 4-1-d
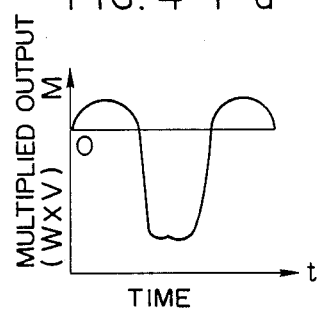
FIG. 4-1-e
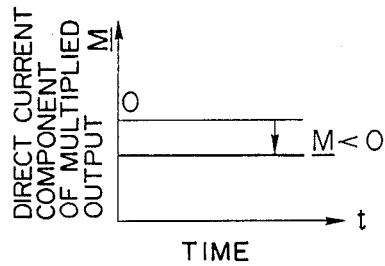

FIG. 4-2-a 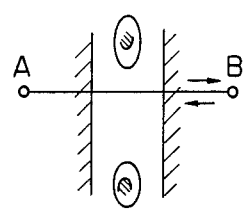
FIG. 4-2-b 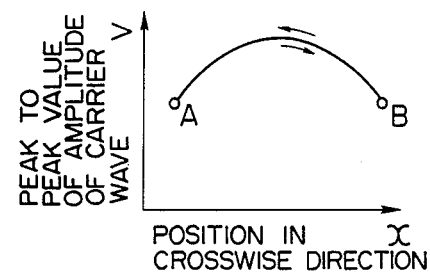
FIG. 4-2-c 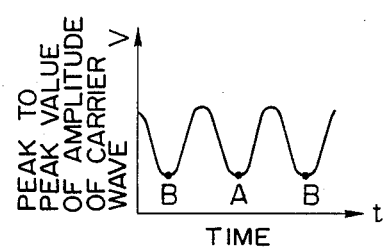
FIG. 4-2-d 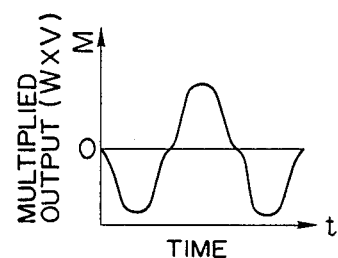
FIG. 4-2-e 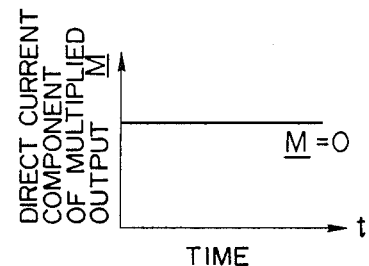

FIG.4-3-a
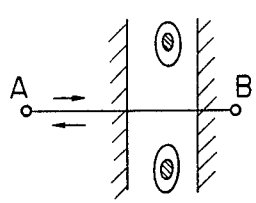
FIG.4-3-b
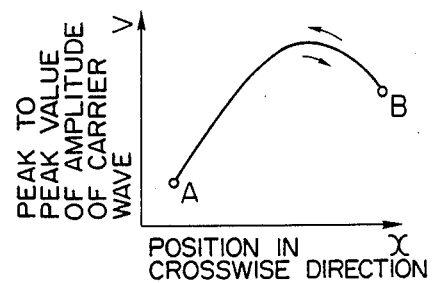
FIG.4-3-c
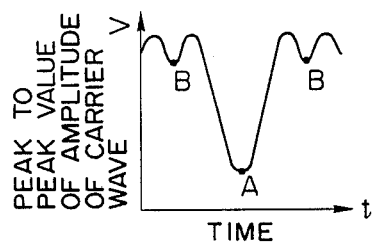
FIG.4-3-d
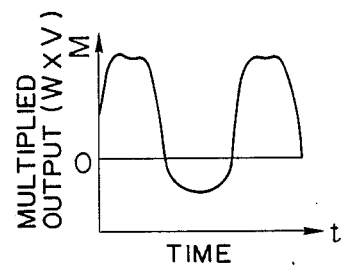
FIG.4-3-e
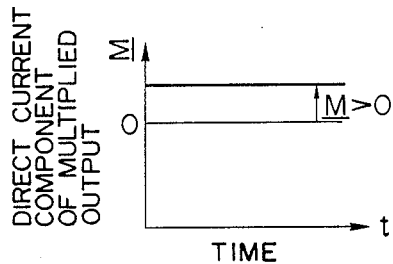
FIG.4-4
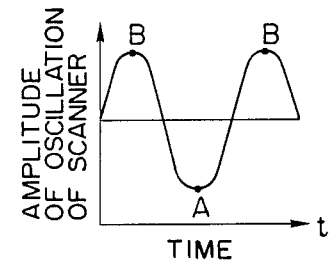

FIG. 5-1-a
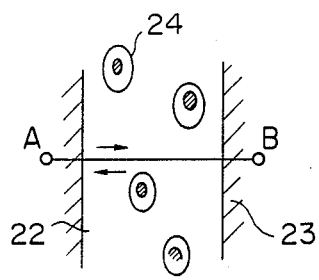
FIG. 5-1-b
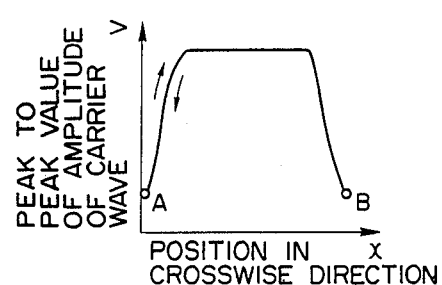
FIG. 5-1-c
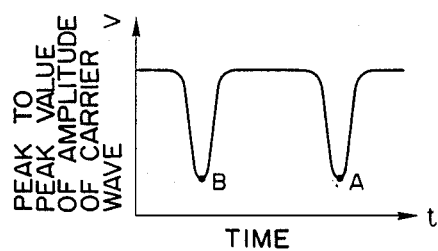
FIG. 5-1-d
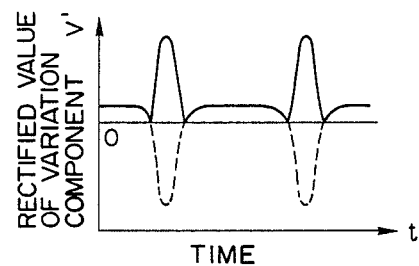
FIG. 5-1-e
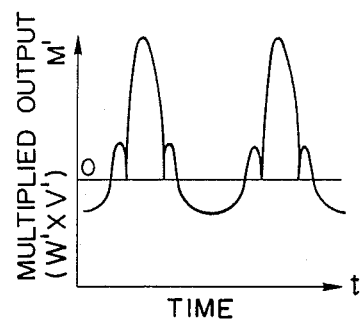
FIG. 5-1-f
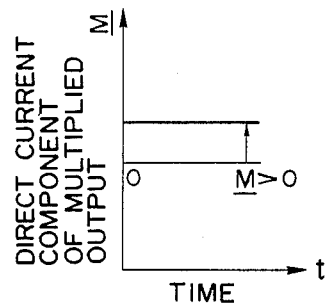

FIG.5-2-a
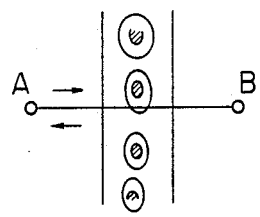
FIG.5-2-b
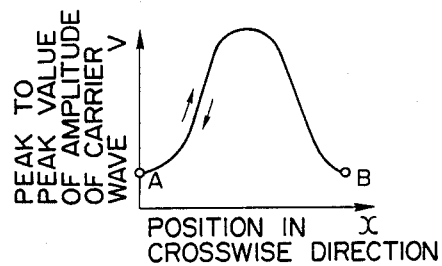
FIG.5-2-c
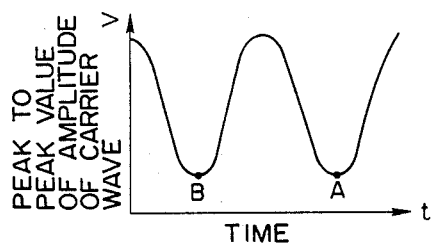
FIG.5-2-d
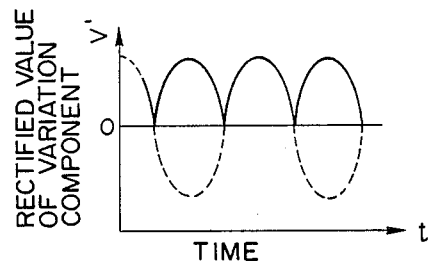
FIG.5-2-e
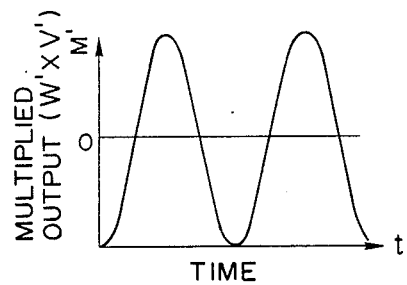
FIG.5-2-f
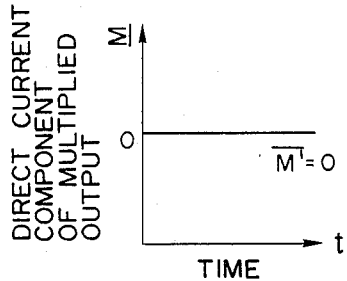

FIG. 5-3-a
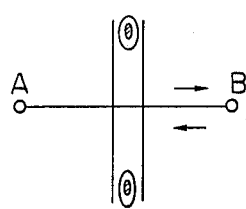
FIG. 5-3-b
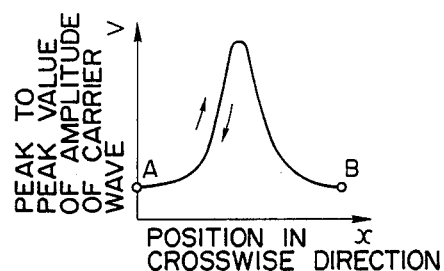
FIG. 5-3-c
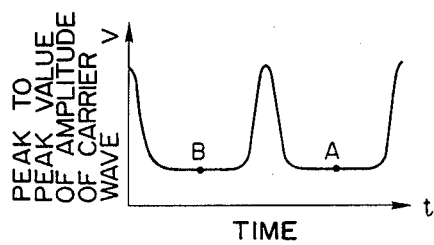
FIG. 5-3-d
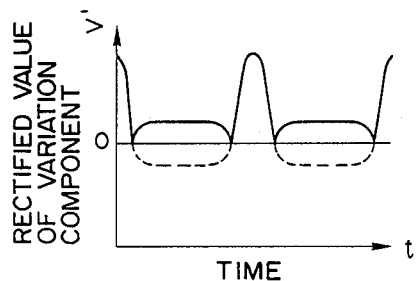
FIG. 5-3-e
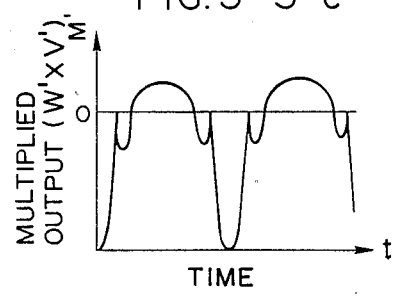
FIG. 5-3-f
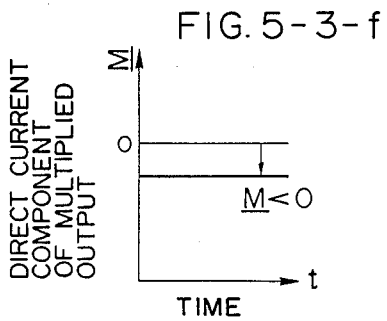
FIG. 5-4
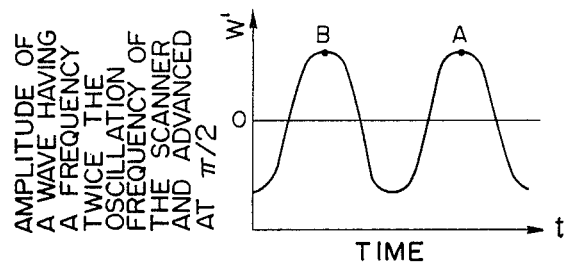

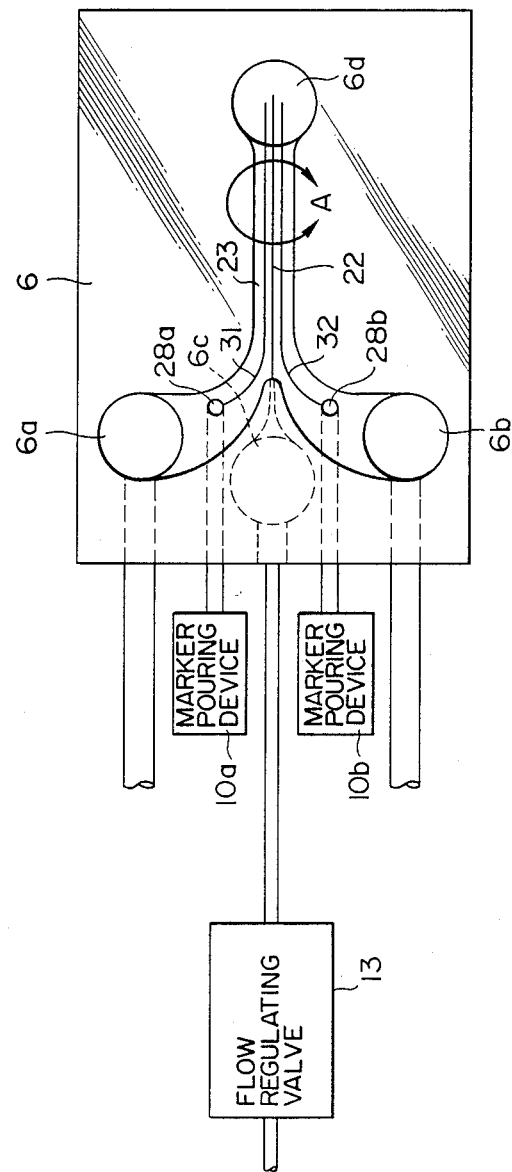

PHOTOANALYSIS APPARATUS WITH MEANS FOR CORRECTING FLOW RATE OF FLUID CARRYING PARTICLES AND/OR POSITION OF APPLIED LIGHT BEAM FOR EXAMINATION AND PHOTOANALYSIS METHOD THEREFOR

BACKGROUND OF THE INVENTION

The present invention relates to a sheath flow type photoanalysis apparatus in which fluid carrying particles such as cells flows in laminar conditions surrounded by sheath fluid through a capillary tube, a light beam having a constant wave length is applied on the flow of the fluid carrying particles, and properties of the particles such as kind, size, number and shape are measured from strength of light scattering and/or fluorescence caused by the particles and, more particularly, to a sheath flow type photoanalysis apparatus with means for correcting a position of the applied light beam for examination and the flow rate of the fluid carrying particles.

The present invention also relates to a method for correcting a position on which a light beam for examination is applied flow rate of fluid carrying particles in photoanalysis apparatus.

For example, U.S. Pat. No. 3,873,204, SCIENCE (Vol. 150, pp. 630-631, October, 1965), and Rev. Sci. Instrum. (Vol. 46, pp. 1021-1024, No. 8, August, 1975) have disclosed the photoanalysis apparatus in which fluid carrying particles such as cells flows through a capillary tube in laminar conditions surrounded by the sheath fluid, a light beam having a constant wave length is applied on the flow of the fluid carrying particles, and properties of the particles such as kind, size, number and shape are measured from strength of light scattering and/or fluorescence caused by the particles.

In the above-mentioned prior arts, flow of fluid carrying pilot particles such as control cells (for example, spherical cells such as blood of a chicken) or reference particles (spherical artificial particles) are subjected to optical measurement before the subject examination of particles starts and, from the result of the measurement an appropriate position on which the light beam for examination is applied is experientially determined. That is to say, since the flow rate of the fluid carrying particles to be examined is preset by utilizing the pilot particles which are different from the actual particles to be examined, the conventional method lacks reliability. Further, the operations for deciding the position on which the light beam is applied become thus tedious and complicated. When a difference in position occurs between the position on which the light beam for examination is applied and the flow of the fluid carrying particles by any disturbance during the actual examination of the particles, it is almost impossible to correct such a difference in position with the examination being continued.

In order to conduct the optimum optical measurement, it is necessary that the particles carried in the fluid flow through a spot of the light beam for examination. Thus, a width of the flow of the fluid carrying particles should appropriately be maintained constant. The width of the fluid carrying particles depends on its flow rate. Accordingly, there exists an optimum value to the flow rate of the fluid carrying particles in order to conduct an optimum optical measurement. Whereas, in the prior arts, the pilot particles are streamed prior to the examination of the particles to be examined and, the optimum value of the flow rate is supposed to be determined from the results of the optical measurement of the strength of light scattering and/or fluorescence caused by the pilot particles. Since the flow rate of the fluid carrying particles is determined by the pilot particles different from the actual particles to be examined, the prior art method has poor reliability. Further, the prior art method has a disadvantage that when a variation of the flow rate is occurred by any cause during the examination, it is not possible to correct the variation of the flow rate during the examination.

SUMMARY OF THE INVENTION

Accordingly, one object of the invention is to provide a sheath flow type photoanalysis apparatus which is capable of deciding a position on which a light beam for examination is applied without using pilot particles and of automatically correcting a difference in position between the light beam for examination and a fluid carrying particles during the examination of the particles.

A further object of the present invention is to provide a sheath flow type photoanalysis apparatus which is capable of deciding the flow rate of fluid carrying particles without using pilot particles and of automatically correcting the flow rate of the fluid carrying particles to a predetermined flow rate during the examination.

A sheath flow type photoanalysis apparatus according to the present invention is characterized in that it comprises marker pouring means for pouring markers into one of sheath fluid and fluid carrying particles in a flow-cell device, the markers emitting fluorescence or light scattering when received a light beam for correction; optical means for applying the light beam for correction to the markers in the flow-cell device to measure strength of fluorescence or light scattering caused by the markers to generate a signal for correction; signal processing means for calculating from the signal for correction at least one of a difference in position between a center of the fluid carrying particles in the flow-cell device and a center of the light beam for examination and a difference in flow rate between a predetermined flow rate and an actual flow rate of the fluid carrying particles to generate correspondingly at least one of a command signal for position correction and a command signal for flow rate correction; and correspondingly at least one of first correcting means for shifting the center of the light beam for examination to the center of the fluid carrying particles in accordance with the command signal for position correction and second correcting means for correcting the flow rate of the fluid carrying particles in the flow-cell device to the predetermined flow rate in accordance with the command signal for flow rate correction.

In one embodiment of the present invention, the marker pouring means includes an opening opened in the flow of the fluid carrying particles; the optical means comprises a scanner with a scanner mirror which is disposed between a lamp and a condenser lens for oscillating the light beam for examination in crosswise direction of the flow of the fluid carrying particles within a predetermined angle, a first flat half mirror disposed between the scanner mirror and the condenser lens, the first flat half mirror permitting the light beam for examination to pass therethrough and reflecting a light beam from opposite direction of the light beam for examination, a curved half mirror disposed between the first flat half mirror and the condenser lens, whose concave surface is faced toward the condenser lens, the curved half mirror permitting a part of the light beam for examination to pass therethrough and reflecting a remaining part of the light beam for examination, a second flat half mirror disposed between an objective lens and a first photo-detector, which reflects only fluorescence or light scattering caused by the markers in the fluid carrying particles, and a second photo-detector for detecting the fluorescence or light scattering reflected by the second flat half mirror to generate a signal for correction; the first correcting means comprising a scanner controller to control the scanner to change a center of the oscillation in accordance with said first command signal; and the second correcting means comprising a valve controller to control a flow control valve to correct the flow rate of the fluid carrying particles in the flow-cell device in accordance with the second command signal.

In another embodiment of the present invention, the marker pouring means includes two openings respectively opened at each side of the flow of the fluid carrying particles in the flow-cell device to pour from these two openings different markers which emit fluorescence or light scattering whose wave lengths are different from each other; the second optical means comprises a mirror disposed between the lamp and the condenser lens, the mirror being rotatable so as to move the light beam for examination in crosswise direction of the flow of the fluid carrying particles, a diffraction grating disposed between the mirror and the flow-cell device for separating two light beams for correction from the light beam for examination, the two light beams for correction respectively being applied on the markers, a flat half mirror disposed between the objective lens and the first photo-detector, the flat half mirror reflecting only fluorescence or light scattering caused by the markers in the sheath fluid, and a second photo-detector for detecting the fluorescence or light scattering reflected by the flat half mirror to generate the signal for correction; the first correcting means comprises a controller for moving the mirror in accordance with the first command signal; and the second correcting means comprises a valve controller to control the flow control valve to correct the flow rate of the fluid carrying particles in the flow-cell device in accordance with the second command signal.

A method for correcting a difference in position between a center of flow of fluid carrying particles and a center of a light beam for examination in a sheath flow type photoanalysis apparatus according to the invention comprises: pouring markers which emit fluorescence or light scattering having a constant wave length when received a light beam; oscillating the light beam for examination in crosswise direction of the flow of the fluid carrying particles; detecting strength of the fluorescence or light scattering caused by the markers in the fluid carrying particles to generate a signal for correction; calculating a difference in position between a center of the fluid carrying particles in the flow-cell means and a center of the oscillation of the light beam for examination on the basis of the signal for correction to generate a command signal for position correction; and shifting the center of the light beam for examination to the center of the fluid carrying particles in accordance with the command signal.

Another method for correcting a difference in position between a center of flow of fluid carrying particles and a center of a light beam for examination in a sheath flow type photoanalysis apparatus according to the invention comprises: pouring different markers, which emit fluorescence or light scattering having constant wave lengths different from each other when received a light beam, into sheath fluid at each side of the flow of the fluid carrying particles; separating two light beams for correction from the light beam for examination by means of a diffraction grating to respectively apply onto the markers at each side of the fluid carrying particles in such a manner that centers of the two light beams for correction are offset from centers of the flow of the markers in a direction opposite to each other; detecting strength of the fluorescence or light scattering caused by the markers in the sheath fluid to generate a signal for correction; calculating a difference in position between a center of the fluid carrying particles in the flow-cell means and a center of the light beam for examination on the basis of the signal for correction to generate a command signal for position correction; and shifting the center of the light beam for examination to the center of the fluid carrying particles in accordance with the command signal.

A method for correcting flow rate of flow of fluid carrying particles in a sheath flow type photoanalysis apparatus according to the invention comprises: pouring markers, which emit fluorescence or light scattering having a constant wave length when received a light beam, into the fluid carrying particles; oscillating the light beam for examination in crosswise direction of the flow of the fluid carrying particles; detecting strength of the fluorescence or light scattering caused by the marker in the fluid carrying particles to generate a signal for correction; calculating a difference in the flow rate between a predetermined flow rate and an actual flow rate of the fluid carrying particles on the basis of the signal for correction to generate a command signal for flow rate correction; and correcting the flow rate of the fluid carrying particles to the predetermined flow rate in accordance with the command signal.

Another method for correcting flow rate of flow of fluid carrying particles in a sheath flow type photoanalysis apparatus according to the invention comprises: pouring different markers, which emit fluorescence or light scattering having constant wave lengths different from each other when received a light beam, into a sheath fluid at each side of the flow of the fluid carrying particles; separating two light beams for correction from the light beam for examination by means of a diffraction grating to respectively apply these two light beams on the markers at each side of the fluid carrying particles in such a manner that centers of the two light beams for correction are offset from centers of the flows of the markers opposite to each other; detecting strength of the fluorescence or light scattering caused by the markers in the sheath fluid to generate a signal for correction; calculating a difference in flow rate between a predetermined flow rate and an actual flow rate of the fluid carrying particles on the basis of the signal for correction to generate a command signal for flow rate correction; and correcting the flow rate of the fluid carrying particles to the predetermined flow rate in accordance with the command signal.

BRIEF DESCRIPTION OF THE DRAWINGS

FIGS. 4-1-a~e, FIGS. 4-2-a~e, FIGS. 4-3-a~e, and FIG. 4—4 are illustrative views and graphs, which explain a method for correcting a difference in position between a center of flow of fluid carrying particles and a center of a light beam for examination in the apparatus of one embodiment of the present invention, respectively;

FIGS. 5-1-a~e, FIGS. 5-2-a~e, FIGS. 5-3-a~e, and FIG. 5-4 are illustrative views and graphs, which explain a method for correcting flow rate of the fluid carrying particles in the apparatus of one embodiment of the present invention, respectively;

FIG. 7 is a schematically illustrated plan view of a flow-cell device used for the embodiment in FIG. 6.

DETAILED DESCRIPTION OF THE PREFERRED EMBODIMENTS

Figure 1:
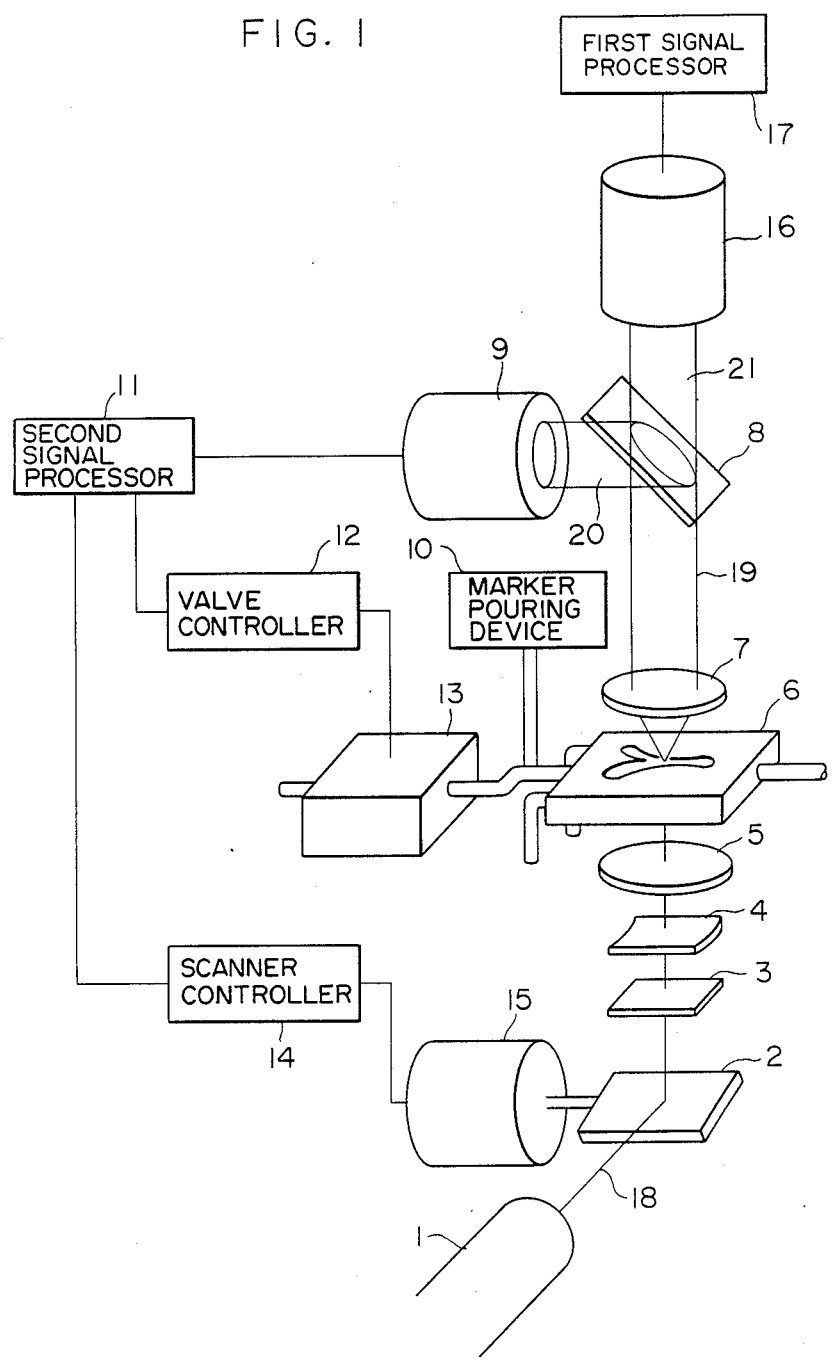
FIG. 1 is a schematically illustrated explanatory view showing one embodiment of a sheath flow type photoanalysis apparatus according to the present invention.

One embodiment of the sheath flow type photoanalysis apparatus according to the present invention will be described hereinafter with reference to FIGS. 1-5.

A flow-cell device 6 includes two inlet openings 6a, 6b for sheath fluid 23, an inlet opening 6c for fluid 22 carrying particles formed between these two inlet openings and a fluid outlet opening 6d and the fluid 22 carrying particles is surrounded by the sheath fluid 23 and is made to flow through the flow-cell device 6 in laminar conditions. Connected to the inlet opening 6c for the fluid 22 carrying particles are a flow regulating valve 13 which controls a flow rate of the fluid 22 carrying particles and marker pouring device 10 which pours markers into the fluid 22 carrying particles. The markers are of fluorescence materials which emit fluorescence having a constant wave length different from those of fluorescence emitted by the particles in the fluid carrying particles when received a light beam. Upper and lower surfaces of the flow-cell device 6 are transparent so that the light beam can pass through. On one side of the flow-cell device 6, there is provided a lamp 1 emitting the light beam 18 for examination. A scanner mirror 2 is connected to a scanner 15 and structured so as to oscillate the light beam 18 for examination projected from the lamp 1 at high frequency in crosswise direction of the flow of the fluid 22 carrying particles in the flow-cell device 6. A condenser lens 5 is disposed on an optical axis of the light beam 18 for examination between the scanner mirror 2 and the flow-cell device 6 so as to condense the light beam 18 for examination to the fluid 22 carrying particles which flows through the flow-cell device 6 in laminar conditions. A first flat half mirror 3 is disposed between the scanner mirror 2 and the condenser lens 5 and is structured to permit the light beam for the examination supplied from the side of the scanner mirror 2 to pass therethrough and, on the contrary, to reflect a light beam from the opposite direction. A curved half mirror 4 is interposed between the first flat half mirror 3 and the flow-cell device 6 in such a manner that its concave surface is faced toward the flow-cell device 6, and a center line of the curve extends parallel to the flow of the fluid 22 carrying particles in the flow-cell device 6. This curved half mirror 4 is such arranged that a part of the light beam from the side of the first flat half mirror 3 is reflected therefrom and a remaining part of the light beam passes therethrough.

An objective lens 7 is provided on the side opposite to the condenser lens 5 of the flow-cell device 6 in order to collect a light beam 19 containing fluorescence 20 from the markers poured into the fluid 22 carrying particles and light scattering and/or fluorescence 21 from the particles 24 in the fluid 22 carrying particles. A second flat half mirror 8 is provided on the downstream side of the objective lens 7. The second flat half mirror 8 allows the light scattering and/or the fluorescence 21 caused by the particles 24 in the fluid 22 carrying particles in a light beam 19 collected by the objective lens 7 to pass therethrough. That is to say, the collected light beam 19 is separated into the light scattering and/or the fluorescence 21 for examination of the particles and the fluorescence 20 for correction. A first photo-detector 16 is located at the downstream side of the second flat half mirror 8 and detects the strength of the light scattering and/or the fluorescence 21 for examination passed through the second flat half mirror 8 to convert it into the signal for examination. A first signal processor 17 is connected to the first photo-detector 16 to analysis with the signal from the first photo-detector 16 some properties of the particles 24 in the fluid 22 carrying particles.

A second photo-detector 9 is placed adjacent to the second flat half mirror 8 and detects the strength of the fluorescence 20 for correction separated by the second flat half mirror 8 to generate a signal for correction. A second signal processor 11 is connected to the second photo-detector 9 and, on the basis of the signal for correction from the second photo-detector 9, it calculates a difference in position between a center of the fluid 22 carrying particles in the flow-cell device 6 and a center of the oscillation of the light beam 18 for examination to generate a command signal for correction and also a difference in flow rate between the predetermined flow rate and an actual flow rate of the fluid 22 carrying particles in the flow-cell device to generate a command signal for flow rate correction. Connected to the second signal processor 11 are a valve controller 12 for controlling a flow regulating valve 13 and a scanner controller 14 for controlling the oscillation of the scanner 15. The valve controller 12 controls in accordance with the command signal for flow rate correction the flow regulating valve 13 to correct the flow rate of the fluid 22 carrying particles in the flow-cell device 6 and the scanner controller 14 controls in accordance with the command signal for position correction to correct a center of the oscillation of the light beam 18 for examination toward a center of the flow of the fluid 22 carrying particles in the flow-cell device.

The light beam 18 for examination emitted from the lamp 1 is oscillated to the extent not causing variation of the light scattering and/or fluorescence for examination. In other words, the light beam 18 for examination is oscillated only within a very small angle $\alpha$ to the extent that the particles 24 in the carrying fluid 22 may not deviate out of the spot of the light beam 18 for examination. The light beam 18 for examination passes through the first flat half mirror 3 and the curved half mirror 4 and is applied to the fluid 22 carrying particles in the flow-cell device 6. At this time, parts 25 of the light beam 18 for examination are reflected by the curved half mirror 4 and then are again reflected by the first flat half mirror 3 to pass through the curved half mirror 4 with being attenuated at a certain extent and finally are applied on locations remote from the flow of the fluid 22 carrying particles in crosswise direction. That is to say, the light beam for correction is an oscillated light beam for examination. As the second flat half mirror 8 permits only the light scattering and/or the fluorescence 21 caused by the particles 24 in the fluid 22 to pass therethrough, the fluorescence 20 caused by the markers is transmitted to the second photo-detector 9. Then the transmitted fluorescence 20 is converted into a signal for correction as amplitude modulation of a carrier wave caused by an oscillator included within the second photo-detector 9. The signal for correction is input in the second signal processor 11, and delivered to one processing system which calculates a difference in position between the center of the flow of the fluid 22 carrying particles and the center of the oscillation of the light beam 18 for examination to generate a command signal for position correction, and to the other processing system which calculates a difference in flow rate between the predetermined flow rate and the actual flow rate of the fluid 22 carrying particles to generate a command signal for flow rate correction.

Figure 2:
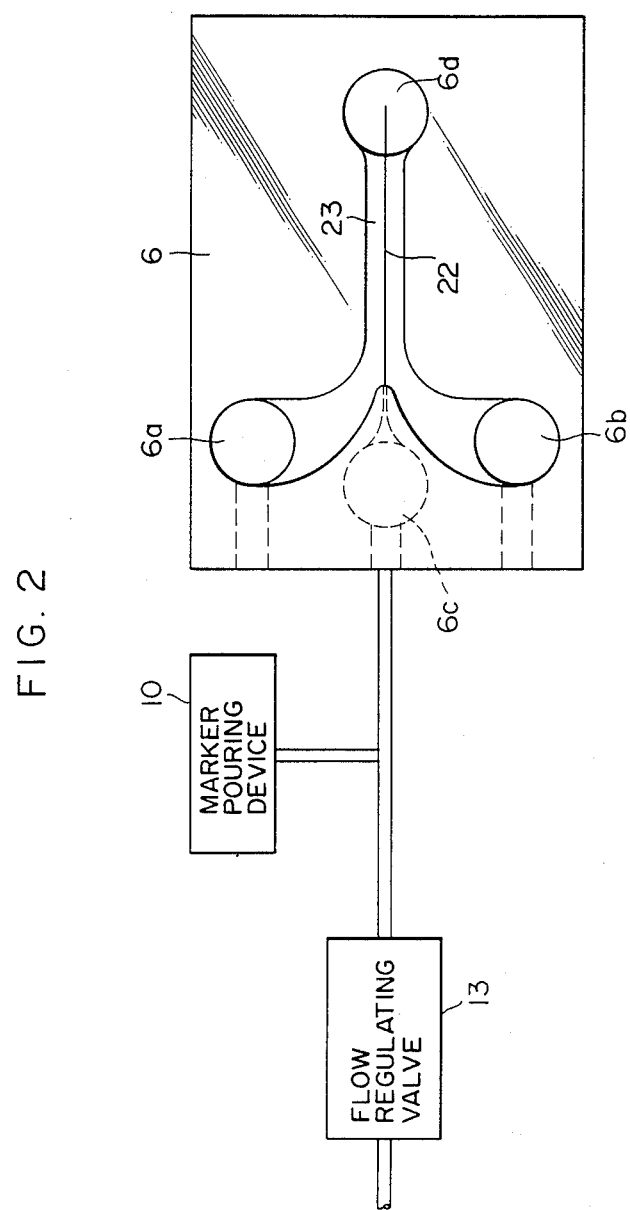
FIG. 2 is a schematically illustrated plan view of a flow-cell device incorporated in the embodiment shown in FIG. 1.
Figure 3:
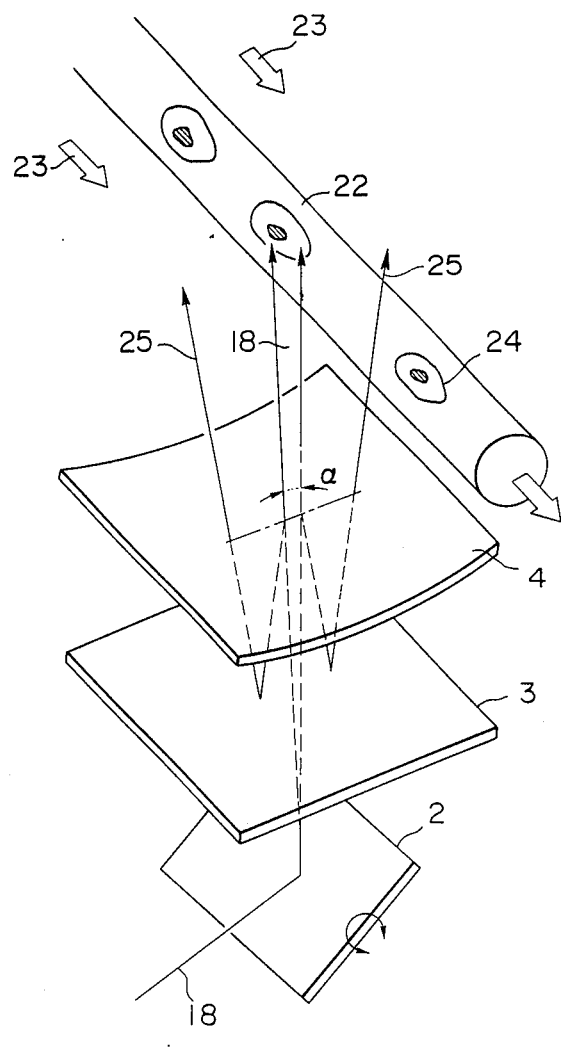
FIG. 3 is an enlarged view of an essential portion of the embodiment shown in FIG. 1, illustrating the operations of the photoanalysis apparatus, in which a condenser lens, the main body of the flow-cell device, a scanner and some others are conveniently omitted for clarification.

The correcting steps in the processing system for position correction will be explained with reference to FIGS. 4-1-$a \sim e$, FIGS. 4-2-$a \sim e$, FIGS. 4-3$a \sim e$, and FIGS. 4—4. When the reflected light beam 25 is oscillated between a point A and a point B, as shown in FIG. 4-1-$a$, it is assumed that the fluid 22 carrying particles is shifted to the side of A, as shown in the same drawing. At the moment, a peak value V of amplitude of carrier wave of the signal for correction varies between both A and B points as shown in FIG. 4-1-$b$. When the abscissa is set as the axis of time t, the peak to peak value V turns into FIG. 4-1-$c$. When this peak to peak value V is multiplied by an oscillation amplitude W (FIG. 4—4) of the scanner 15 through an analog multiplier, an output M as shown in FIG. 4-1-$d$ is obtainable. When a direct current component is taken out from the output M while passing through a high-frequency cut filter, a negative value is obtained as shown in FIG. 4-1-$e$.

When the same procedures as in FIGS. 4-1-$a \sim e$ are applied to a case in which the fluid 22 carrying particles flows at a center of the A-B points (FIGS. 4-2-$a \sim e$) and a case in which the fluid 22 carrying particles flows at a side of B point between the A-B points, respective outputs M=0 and M>0 can be obtained.

When the output M is used to impress as a voltage controlling a center of amplitude of the scanner controller 14 through an amplifier, it becomes possible to register the center of the amplitude between the points A and B automatically with the center of the flow of the fluid 22 carrying particles. That is to say, the light beam 18 for examination is continuously applied to the center of the flow of the fluid 22 carrying particles without using the pilot particles.

The correcting steps in the processing system for the flow rate correction will be explained with reference to FIGS. 5-1-$a \sim f$, FIGS. 5-2-$a \sim f$, FIGS. 5-3-$a \sim f$, and FIG. 5-4. When the reflected light beam 25 is oscillated between a point A and a point B, as shown in FIG. 5-1-$a$, it is assumed that the fluid 22 carrying particles is increased in flow rate and is enlarged in width, as shown in the same drawing. At the moment, a peak to peak value V of the carrier wave of the signal for correction varies between both A and B points such as shown in FIG. 5-1-$b$. When the abscissa is set as the axis of time t, the peak to peak value V turns into a signal shown in FIG. 5-1-$c$. When a direct current component is taken out from this signal and a negative value is reversed into a positive value, that is, a variation component of the signal is rectified, a signal V' (FIG. 5-1-$d$) is obtained. When this signal V' is multiplied by an amplitude W' (FIG. 5-4) of a wave which has a frequency twice the oscillation frequency of the scanner 15 and advanced at x/2 through the analog multiplier, an output M' as shown in FIG. 5-1-$e$ is obtained. When a direct current component is taken out from the output M' by means of a high-frequency cut filter, a positive output M' is obtained as shown in FIG. 5-1-$f$.

The same procedures as in FIGS. 5-1-$b \sim f$ are applied to a case in which the flow rate of the fluid 22 carrying particles substantially equals to a predetermined value (FIGS. 5-2-$a \sim f$) and a case in which the flow rate is less than such a predetermined value (FIGS. 5-3-$a \sim f$), respective outputs M'=0 and M'<0 can be obtained.

When this output M' is used to impress as a voltage driving the valve controller 12 through the amplifier, the flow rate of the fluid 22 carrying particles can be automatically maintained at the predetermined flow rate. Further, by changing the oscillation amplitude between the A-B points, a predetermined flow rate of the fluid 22 carrying particles can be freely selected.

When the oscillation frequency of the scanner mirror 2 is set at a high frequency such as 1 KHz, it is possible to shift the center of the light beam for examination 18 to the center of the flow of the fluid 22 carrying particles with a high responsibility even if the flow of the fluid carrying particles is shifted by any turburance to the flow-cell device 6, clogging of the flow system and the like.

The control operations such as adjustment of the optical axes before the examination may be almost eliminated.

Figure 6:
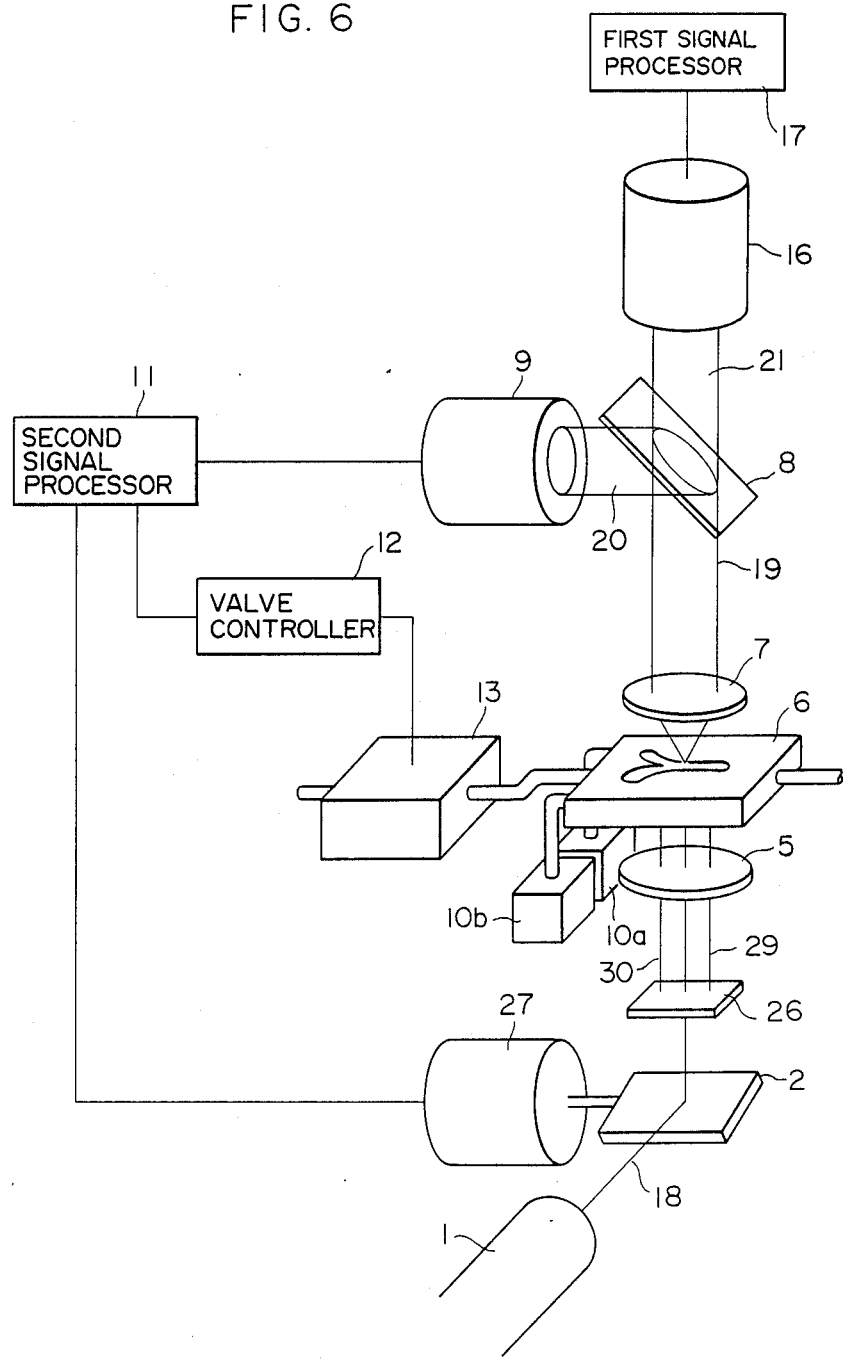
FIG. 6 is a schematically illustrated explanatory view showing another embodiment of the sheath flow type photoanalysis apparatus according to the present invention.

Next, another embodiment of the sheath flow type photoanalysis apparatus according to the present invention will be described hereinafter with reference to FIGS. 6-8. Explanations to the same portions coincident with those in the embodiment of FIG. 1 will be omitted.

The flow-cell device 6 includes two inlet openings 6$a$, 6$b$ for the sheath fluid 23, an inlet opening 6$c$ for the fluid 22 carrying particles formed between these two inlet openings, two inlet openings 28$a$, 28$b$ for the markers each provided in a flow passage for the sheath fluid and the fluid outlet opening 6$d$. A flow regulating valve 13 which controls flow rate of the fluid carrying particles is connected to the inlet opening 6$c$ for the fluid carrying particles. Further, marker pouring devices 10$a$, 10$b$ which pour the markers into the sheath fluid 23 are connected to the inlet openings 28$a$, 28$b$ for the markers, so that flows 31, 32 of the markers are provided at both sides of the fluid 22 carrying particles. The markers poured through the marker pouring device 10$a$, 10$b$ are different markers which emit fluorescence having constant wave lengths different from each other when received a high beam. The reason why the wave lengths are made to be different from each other is to make it possible to detect a direction of difference in position between the fluid 22 carrying particles and the light beam 18 for examination.

Figure 8A:
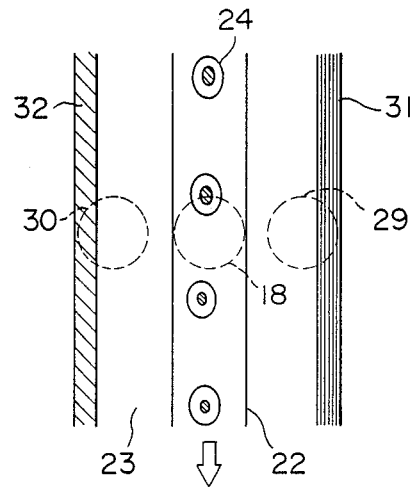
FIG. 8a and FIG. 8b are enlarged views of a portion A in FIG. 7, each showing an applying mode of the light beam for correction to the flow of markers in the sheath fluid.
Figure 8B:
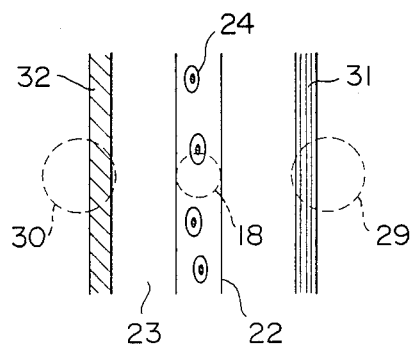

Although, in the above-mentioned embodiment there are provided the first flat half mirror 3 and the curved half mirror 4 between the scanner mirror 2 and the condenser lens 5, this embodiment includes a diffraction grating 26 by which two light beams 29, 30 for correction are separated from the light beam 18 for examination and applied to the sheath fluid 23 in the flow-cell device 6. The light beams 29, 30 for correction are applied in such a manner that centers of the light beams 29, 30 for correction are offset from centers of flow of the markers 31, 32 in a direction opposite to each other as shown in FIGS. 8a and 8b. A controller 27 is connected to the scanner mirror 2 to rotatably move the scanner mirror 2 in accordance with the command signal for position correction from the signal processor 11. That is to say, an optical axis of the light beam 18 for examination is movable by the rotational movement of the scanner mirror 2 in a direction perpendicular to the flow of the fluid 22 carrying particles in the flow-cell device 6.

The correcting process will be explained by taking a case as an example in which a manner of the light beams for correction applied is in the manner shown in FIG. 8a.

When a position of the flow of the fluid 22 carrying particles is shifted rightwardly of the drawing, the flow 31 of the markers goes out of the spot of the light beam 29 for correction, whereas the flow 32 of the markers comes into the spot of the light beam 30 for correction. As a result, the fluorescence from the flow 31 of the markers is decreased in strength, while the fluorescence from the flow 32 of the markers is increased in strength. When a position of the flow of the fluid 22 carrying particles is shifted leftwardly of FIG. 8a, the flow 31 of the markers comes into the spot of the light beam 29 for correction, whereas the flow 32 of the markers goes out of the spot of the light beam 30 for correction. As a result, the fluorescence from the flow 31 of the markers is increased in strength, while the fluorescence of the markers is decreased in strength. Since, as mentioned above, there exists the difference in wave length between the fluorescence from one markers 31 and fluorescence from the other markers 32, each fluorescence can thus be distinguished mutually. Thus when the variation in strength of the fluorescence is measured, an offset direction and a difference in position between the center of the light beam 18 for examination and the center of the flow of the fluid 22 carrying particles can be detected. These fluorescence is separated by the half mirror 8 from the light beam 19 which is collected through the objective lens 7 and, the separated fluorescence is transmitted to the second photo-detector 9 and converted into a signal for correction. The signal processor 11 connected to the second photo-detector 9 calculates from the signal for correction the offset direction and the difference in position between the center of the flow of the fluid 22 carrying particles in the flow-cell device 6 and the center of the light beam 18 for examination and, then, it outputs a command signal for position correction to the controller 27. The controller 27 rotates the scanner mirror 2 in accordance with the command signal for position correction to shift the center of the light beam 18 for examination toward the center of the flow of the fluid 22 carrying particles 18.

When the flow rate of the fluid 22 carrying particles increases, both flows 31 and 32 of the markers are moved away from each other so that the flows 31, 32 of the markers go out of the respective spots of the light beams for correction 29, 30. The fluorescence from the both markers are thus weakened in strength at the same time. Furthermore, when the flow rate of the fluid 22 carrying particles decreases, the flows 31 and 32 of the markers approach to each other so that both flows 31, 32 come into the spots of the light beams 29, 30 for correction. Each strength of the fluorescence from both markers thus increases simultaneously.

With the same manner as described previously, these fluorescence is separated by the half mirror 8 from the light beam 19 which is collected through the objective lens 7 and, the separated fluorescence is transmitted to the second photo-detector 9 and converted into a signal for correction. The signal processor 11 connected to the second photo-detector 9 calculates from the signal for correction the difference in flow rate between the actual flow rate of the fluid 22 carrying particles in the flow-cell device 6 and the predetermined flow rate and, then, it outputs a command signal for flow rate correction to the valve controller 12. The valve controller 12 controls the flow regulating valve 13 in accordance with the command signal for flow rate correction to regulate the flow rate of the fluid 22 carrying particles in the flow-cell device 6 to the predetermined flow rate.

In this embodiment, the applying position of the light beam for examination and the flow rate of the fluid carrying particles can be set without using the pilot particles.

In the above embodiments, the fluorescent materials emitting fluorescence having constant wave lengths when received the light beam have been employed as markers which represent the position and flow rate of the fluid 22 carrying particles, but the reference particles, control cells and the like may, of course, be utilized with such materials.

Also, in the above-mentioned embodiments, although both of the means for position correction and flow rate correction have been accompanied with the apparatus, the apparatus may incorporate either one of these means.

As fully described in hereinbefore, according to the present invention, the applying position of the light beam for examination as well as the flow rate of the fluid carrying particles are determined by means of the subject particles to be examined, thereby substantially eliminating the tedious adjustment operations such as adjustments of the light applying position and flow rate using the pilot particles before the examination.

Further, according to the invention, it is possible to shift the center of the light beam for examination 18 to the center of the flow of the fluid 22 carrying particles with a high responsibility even if the flow of the fluid carrying particles is shifted by any turbulence to the flow-cell device 6 of clogging of the flow system and the like.

Further, according to the invention, it is possible to always maintain the flow rate of the fluid 22 carrying particles at a predetermined flow rate at a position on which the light beam 18 for examination is applied even if causes causing the variation of the flow rate such as clogging of the flow system, reduction of pressure to supply the fluid carrying particles are occurred during the examination.

What is claimed is:

1. A photoanalysis apparatus comprising:

flow-cell means for pouring sheath fluid and fluid carrying particles in laminar flow in which said fluid carrying particles is surrounded by said sheath fluid, said flow-cell means includes a flow-cell device and a flow control valve to control the flow rate of said fluid carrying particles;

first optical means for applying a light beam for examination having a constant wave length on said fluid carrying particles in the flow-cell device to measure strength of light scattering and/or fluorescence caused by said particles in said fluid carrying particles to generate a signal for examination, said first optical means comprising a lamp for emitting said light beam for examination, a condenser lens disposed between said flow-cell device and said lamp, an objective lens disposed on opposite side of said flow-cell device, and a first photo-detector to measure the strength of light scattering and/or fluorescence caused by the particles in the fluid carrying particles to generate the signal for examination;

first signal processing means for processing said signal for examination from said first optical means to detect properties of the particles such as kind, size, number and shape;

marker pouring means for pouring markers into one of said sheath fluid and fluid carrying particles in said flow-cell device, said markers emitting fluorescence or light scattering having a constant wave length when received a light beam for correction;

second optical means for applying the light beam for correction to said markers in said flow-cell device to measure strength of fluorescence or light scattering caused by said markers to generate a signal for correction;

second signal processing means for calculating from said signal for correction at least one of a difference in position between a center of said fluid carrying particles in said flow-cell device and a center of said light beam for examination and a difference in flow rate between a predetermined flow rate and an actual flow rate of said fluid carrying particles in said flow-cell device to generate correspondingly at least one of a first command signal for position correction and a second command signal for flow rate correction; and correspondingly at least one of first correcting means for shifting the center of the light beam for examination to the center of said fluid carrying particles in said flow-cell device in accordance with said first command signal and second correcting means for correcting the flow rate of said fluid carrying particles to the predetermined flow rate in accordance with said second command signal.

2. A photoanalysis apparatus as claimed in claim 1, wherein said marker pouring means includes an opening opened in the flow of said fluid carrying particles, and said second optical means comprises a scanner with a scanner mirror which is disposed between said lamp and said condenser lens for oscillating said light beam for examination in crosswise direction of the flow of the fluid carrying particles within a predetermined angle, said light beam for correction being identical with said oscillated light beam for examination, a first flat half mirror disposed between said scanner mirror and said condenser lens which permits said light beam for examination to pass therethrough and reflects a light beam from opposite direction of said light beam for examination, a curved half mirror disposed between said first flat half mirror and said condenser lens of which concave surface is faced toward said condenser lens, said curved half mirror permitting a part of said light beam for examination to pass therethrough and reflects a part of said light beam for examination, a second flat half mirror disposed between said objective lens and said first photo-detector which reflects only fluorescence or light scattering caused by said markers in said fluid carrying particles, and a second photo-detector for detecting said fluorescence or light scattering reflected by said second flat half mirror to generate said signal for correction, and said first correcting means comprises a scanner controller to control said scanner to change a center of said oscillation in accordance with said first command signal, and said second correcting means comprises a valve controller to control said flow control valve to correct the flow rate of said fluid carrying particles in said flow-cell device in accordance with said second command signal.

3. A photoanalysis apparatus as claimed in claim 1, wherein said marker pouring means includes two openings respectively opened at each side of the flow of the fluid carrying particles in said flow-cell device and pours from said two openings into the sheath fluid different markers which emit fluorescence or light scattering of which wave lengths are different from each other, and said second optical means comprises a mirror disposed between said lamp and said condenser lens, said mirror being rotatable so as to move said light beam for examination in crosswise direction of the flow of the fluid carrying particles, a diffraction grating disposed between said mirror and said flow-cell device for separating two light beam for correction from said light beam for examination, said two light beam for correction respectively being applied on flow of the markers in such a manner that respective centers of the two light beam for correction are offset from respective centers of the flow of the markers in a direction opposite to each other, a flat half mirror disposed between said objective lens and said first photo-detector, said flat half mirror reflecting only fluorescence or light scattering caused by said markers in said sheath fluid, and a second photo-detector for detecting fluorescence or light scattering reflected by said flat half mirror to generate said signal for correction, and said first correcting means comprises a controller for moving said mirror in accordance with said first command signal, and said second correcting means comprises a valve controller to control said flow control valve to correct the flow rate of said fluid carrying particles in said flow-cell device in accordance with said second command signal.

4. A method for correcting a difference in position between a center of flow of fluid carrying particles and a center of a light beam for examination in a photoanalysis apparatus which comprises flow-cell means for pouring sheath fluid and the fluid carrying particles in laminar flow in which the fluid carrying particles is surrounded by the sheath fluid, optical means for applying the light beam for examination having a constant wave length on the fluid carrying particles in the flow-cell means to measure strength of light scattering and/or fluorescence caused by the particles in the fluid carrying particles to generate a signal for examination, and signal processing means for processing the signal for examination from the optical means to detect properties of the particles such as kind, size, number and shape, said method comprising:

pouring markers which emit fluorescence or light scattering having a constant wave length when received a light beam into the fluid carrying particles;

oscillating said light beam for examination in crosswise direction of the flow of the fluid carrying particles within a predetermined angle;

detecting strength of the fluorescence or light scattering caused by said markers in the fluid carrying particles to generate a signal for correction;

calculating a difference in position between a center of the fluid carrying particles in the flow-cell means and a center of the oscillation of said light beam for examination on the basis of said signal for correction to generate a command signal for position correction; and shifting the center of the light beam for examination to the center of the fluid carrying particles in the flow-cell means in accordance with said command signal.

5. A method for correcting flow rate of flow of fluid carrying particles in a photoanalysis apparatus which comprises flow-cell means for pouring sheath fluid and the fluid carrying particles in laminar flow in which the fluid carrying particles is surrounded by the sheath fluid, optical means for applying a light beam for examination having a constant wave length on the fluid carrying particles in the flow-cell means to measure strength of light scattering and/or fluorescence caused by the particles in the fluid carrying particles to generate a signal for examination, and signal processing means for processing the signal for examination from the optical means to detect properties of the particles such as kind, size, number and shape, said method comprising:

pouring markers which emit fluorescence or light scattering having a constant wave length when received a light beam into the fluid carrying particles;

oscillating said light beam for examination in crosswise direction of the flow of the fluid carrying particles within a predetermined angle;

detecting strength of the fluorescence or light scattering caused by said markers in the fluid carrying particles to generate a signal for correction;

calculating a difference in flow rate between a predetermined flow rate and an actual flow rate of said fluid carrying particles on the basis of said signal for correction to generate a command signal for flow rate correction; and correcting the flow rate of the fluid carrying particles to the predetermined flow rate in accordance with said command signal.

6. A method for correcting a difference in position between a center of flow of fluid carrying particles and a center of a light beam for examination in a photoanalysis apparatus which comprises flow-cell means for pouring sheath fluid and the fluid carrying particles in laminar flow in which the fluid carrying particles is surrounded by the sheath fluid, optical means for applying the light beam for examination having a constant wave length on the fluid carrying particles in the flow-cell means to measure strength of light scattering and/or fluorescence caused by the particles in the fluid carrying particles to generate a signal for examination, and signal processing means for processing the signal for examination from the optical means to detect properties of the particles such as kind, size, number and shape, said method comprising:

pouring different markers which emit fluorescence or light scattering having constant wave lengths different from each other when received a light beam into the sheath fluid at each side of the flow of the fluid carrying particles;

separating two light beams for correction from said light beam for examination by means of a diffraction grating to respectively apply onto said markers at each side of the fluid carrying particles in such a manner that centers of the two light beam for correction are offset from centers of the flow of the markers in a direction opposite to each other;

detecting strength of the fluorescence or light scattering caused by said markers in the sheath fluid to generate a signal for correction;

calculating a difference in position between a center of the flow of the fluid carrying particles in the flow-cell means and a center of said light beam for examination on the basis of said signal for correction to generate a command signal for position correction; and shifting the center of the light beam for examination to the center of the fluid carrying particles in accordance with said command signal.

7. A method for correcting flow rate of flow of fluid carrying particles in a photoanalysis apparatus which comprises flow-cell means for pouring sheath fluid and the fluid carrying particles in laminar flow in which the fluid carrying particles is surrounded by the sheath fluid, optical means for applying a light beam for examination having a constant wave length onto the fluid carrying particles in the flow-cell means to measure strength of light scattering and/or fluorescence caused by the particles in the fluid carrying particles to generate a signal for examination, and signal processing means for processing the signal for examination from the optical means to detect properties of the particles such as kind, size, number and shape, said method comprising;

pouring different markers which emit fluorescence or light scattering having constant wave lengths different from each other when received a light beam into the sheath fluid at each side of the flow of the fluid carrying particles;

separating two light beams for correction from said light beam for examination by means of a diffraction grating to respectively apply onto said markers at each side of the fluid carrying particles in such a manner that centers of the two light beam for correction are offset from centers of the flow of the markers in a direction opposite to each other;

detecting strength of the fluorescence or light scattering caused by said markers in the sheath fluid to generate a signal for correction;

calculating a difference in flow rate between a predetermined flow rate and an actual flow rate of said fluid carrying particles on the basis of said signal for correction to generate a command signal for flow rate correction; and correcting the flow rate of said fluid carrying particles to the predetermined flow rate in accordance with said command signal.

* * * * *